(12) United States Patent
Ishiba et al.

(10) Patent No.: US 11,118,038 B2
(45) Date of Patent: Sep. 14, 2021

(54) LATEX COMPOSITION

(71) Applicant: ZEON CORPORATION, Tokyo (JP)

(72) Inventors: Masatoshi Ishiba, Tokyo (JP); Takashi Iga, Tokyo (JP); Junji Kodemura, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 74 days.

(21) Appl. No.: 16/337,244

(22) PCT Filed: Sep. 19, 2017

(86) PCT No.: PCT/JP2017/033713
§ 371 (c)(1),
(2) Date: Mar. 27, 2019

(87) PCT Pub. No.: WO2018/061867
PCT Pub. Date: Apr. 5, 2018

(65) Prior Publication Data
US 2019/0300685 A1   Oct. 3, 2019

(30) Foreign Application Priority Data

Sep. 29, 2016 (JP) .............................. JP2016-191535

(51) Int. Cl.
| | | |
|---|---|---|
| *C08L 9/10* | (2006.01) | |
| *C08J 5/02* | (2006.01) | |
| *C08K 5/103* | (2006.01) | |
| *C08L 21/02* | (2006.01) | |
| *D21H 17/35* | (2006.01) | |

(52) U.S. Cl.
CPC . *C08L 9/10* (2013.01); *C08J 5/02* (2013.01); *C08K 5/103* (2013.01); *C08L 21/02* (2013.01); *C08J 2309/10* (2013.01); *D21H 17/35* (2013.01)

(58) Field of Classification Search
CPC .... C08L 9/10; C08L 21/02; C08J 5/02; C08K 5/103
See application file for complete search history.

(56) References Cited

U.S. PATENT DOCUMENTS

| | | | | |
|---|---|---|---|---|
| 2002/0058127 | A1* | 5/2002 | Itada | C09J 7/22 428/174 |
| 2005/0266239 | A1* | 12/2005 | Satake | G02F 1/13363 428/354 |
| 2009/0234064 | A1* | 9/2009 | Wang | C08K 5/0008 524/552 |
| 2010/0240817 | A1 | 9/2010 | Joshi et al. | |
| 2014/0141673 | A1* | 5/2014 | Sugihara | H05K 9/009 442/1 |
| 2015/0315358 | A1* | 11/2015 | Yonemoto | C08L 21/00 524/313 |
| 2015/0376322 | A1 | 12/2015 | Nakamura et al. | |
| 2017/0121510 | A1* | 5/2017 | Yamagishi | C08L 9/06 |
| 2019/0106555 | A1 | 4/2019 | Yang et al. | |

FOREIGN PATENT DOCUMENTS

| | | |
|---|---|---|
| CN | 106317329 A1 | 1/2017 |
| JP | 2012-520928 A | 9/2012 |
| WO | 2014/129547 A1 | 8/2014 |
| WO | 2018/043984 A1 | 3/2018 |

OTHER PUBLICATIONS

May 27, 2020 Extended European Search Report issued in European Patent Application No. 17855822.7.
Nov. 21, 2017 International Search Report issued in International Patent Application PCT/JP2017/033713.
Apr. 2, 2019 International Preliminary Report on Patentability issued in International Patent Application No. PCT/JP2017/033713.

* cited by examiner

*Primary Examiner* — John E Uselding
(74) *Attorney, Agent, or Firm* — Oliff PLC

(57) ABSTRACT

A latex composition containing a conjugated diene polymer latex and a medium-chain fatty acid glyceride, wherein a content proportion of the medium-chain fatty acid glyceride is 1 to 40 parts by weight with respect to 100 parts by weight of the conjugated diene polymer. In the present invention, a medium-chain fatty acid forming the medium-chain fatty acid glyceride is preferably a fatty acid having 6 to 18 carbon atoms. In the present invention, the medium-chain fatty acid glyceride is preferably a medium-chain fatty acid triglyceride. The latex composition preferably further contains a crosslinking agent.

10 Claims, No Drawings

LATEX COMPOSITION

TECHNICAL FIELD

The present invention relates to a latex composition, further specifically, to a latex composition capable of giving a molded film such as a dip-molded product having excellent flexibility and excellent tear strength.

BACKGROUND ART

Conventionally, molded films obtained by molding a latex composition containing a natural rubber latex into a film have been known. For example, as such molded films, dip-molded products obtained by dip-molding a latex composition containing a natural rubber latex and used in contact with human bodies, such as nipples, balloons, gloves, balloons, and stalls, are known. However, a natural rubber latex may contain a protein that causes allergic symptoms in human bodies and therefore may be problematic as a molded film that directly contacts the mucosa or organs of living bodies. Therefore, use of a synthetic rubber latex instead of a natural rubber latex has been studied.

For example, Patent Document 1 discloses a latex composition for dip molding using a synthetic polyisoprene or a styrene-isoprene-styrene block copolymer as a synthetic rubber. However, it has been difficult for a dip-molded product produced using a latex composition obtained according to the technique of Patent Document 1 to have improved tear strength while having excellent flexibility.

RELATED ART DOCUMENTS

Patent Documents

Patent Document 1: International Publication No. WO 2014/129547

SUMMARY OF THE INVENTION

Problem to be Solved by the Invention

The present invention has been made in view of such an actual situation described above, and an object thereof is to provide a latex composition capable of giving a molded film such as a dip-molded product having excellent flexibility and excellent tear strength.

Means for Solving the Problem

As a result of dedicated research to achieve the aforementioned object, the inventors have found that the aforementioned object can be achieved by a latex composition containing a medium-chain fatty acid glyceride in addition to a conjugated diene polymer latex at a predetermined proportion, thereby accomplishing the present invention.

That is, the present invention provides a latex composition containing a conjugated diene polymer latex and a medium-chain fatty acid glyceride, wherein a content proportion of the medium-chain fatty acid glyceride is 1 to 40 parts by weight with respect to 100 parts by weight of the conjugated diene polymer.

In the present invention, a medium-chain fatty acid forming the medium-chain fatty acid glyceride is preferably a fatty acid having 6 to 18 carbon atoms.

In the present invention, the medium-chain fatty acid glyceride is preferably a medium-chain fatty acid triglyceride.

In the present invention, the conjugated diene polymer is preferably a synthetic polyisoprene, a styrene-isoprene-styrene block copolymer, or a nitrile group-containing conjugated diene copolymer.

In the present invention, the latex composition preferably further contains a crosslinking agent.

The present invention further provides a molded film consisting of the aforementioned latex composition.

The present invention further provides a packaging structure including: a coating film consisting of the aforementioned latex composition, the coating film bonding at least a part of a first sheet substrate and at least a part of a second sheet substrate to form a laminate, the packaging structure being capable of containing an article to be packaged between the first sheet substrate and the second sheet substrate.

Effects of Invention

The present invention can provide a latex composition capable of giving a molded film such as a dip-molded product having excellent flexibility and excellent tear strength.

DESCRIPTION OF EMBODIMENTS

The latex composition of the present invention contains a conjugated diene polymer latex and a medium-chain fatty acid glyceride, wherein the content proportion of the medium-chain fatty acid glyceride is 1 to 40 parts by weight with respect to 100 parts by weight of the conjugated diene polymer.

Conjugated Diene Polymer Latex

The conjugated diene polymer latex used in the present invention is a conjugated diene polymer latex obtained by polymerizing a monomer mixture containing at least conjugated diene monomer.

The conjugated diene polymer contained in the conjugated diene polymer latex used in the present invention is not specifically limited and may be a homopolymer of a conjugated diene monomer or may be a copolymer of a conjugated diene monomer with another ethylenically unsaturated monomer copolymerizable with the conjugated diene monomer, but examples thereof include a synthetic polyisoprene, a styrene-isoprene-styrene block copolymer (SIS), and a nitrile group-containing conjugated diene copolymer, and the like. Among these, those containing isoprene units such as a synthetic polyisoprene and a SIS are preferable, and a synthetic polyisoprene is particularly preferable.

In the case of using a synthetic polyisoprene as the conjugated diene polymer, a synthetic polyisoprene latex can be used as the conjugated diene polymer latex. The synthetic polyisoprene contained in the synthetic polyisoprene latex may be a homopolymer of isoprene or may be a copolymer of isoprene with other ethylenically unsaturated monomers that are copolymerizable with isoprene. The content of isoprene units in the synthetic polyisoprene is preferably 70 wt % or more, more preferably 90 wt % or more, further preferably 95 wt % or more, particularly preferably 100 wt % (homopolymer of isoprene) with respect to all monomer units, for ease of obtaining a molded film such as dip-molded product that is flex and has excellent tensile strength.

Examples of the other ethylenically unsaturated monomers that are copolymerizable with isoprene include conjugated diene monomers other than isoprene such as butadiene, chloroprene, and 1,3-pentadiene; ethylenically unsaturated nitrile monomers such as acrylonitrile, methacrylonitrile, fumaronitrile, and α-chloroacrylonitrile; vinyl aromatic monomers such as styrene and alkyl styrene; and ethylenically unsaturated carboxylic acid ester monomers such as methyl (meth)acrylate (which means "methyl acrylate and/or methyl methacrylate", and the same hereinafter applies to ethyl (meth)acrylate and the like), ethyl (meth) acrylate, butyl (meth)acrylate, and (meth)acrylic acid-2-ethylhexyl. One of these other ethylenically unsaturated monomers that are copolymerizable with isoprene may be used alone, or a plurality of them may be used in combination.

The synthetic polyisoprene can be obtained by a conventionally known method, for example, by solution polymerization of isoprene with other ethylenically unsaturated copolymerizable monomers used as required, in an inert polymerization solvent, using a Ziegler polymerization catalyst composed of trialkylaluminum-titanium tetrachloride or an alkyl lithium polymerization catalyst such as n-butyl lithium and sec-butyl lithium. The polymer solution of the synthetic polyisoprene obtained by the solution polymerization may be used as it is for producing the synthetic polyisoprene latex as the conjugated diene polymer latex but can be used also for producing the synthetic polyisoprene latex by extracting a solid synthetic polyisoprene from the polymer solution and thereafter dissolving it in an organic solvent.

At this time, impurities such as the residue of the polymerization catalyst remaining in the polymer solution after the synthesis may be removed. Further, an anti-aging agent, which will be described below, may be added into the solution during the polymerization or after the polymerization. Further, a commercially available solid synthetic polyisoprene also can be used.

There are four types of the isoprene units in the synthetic polyisoprene, depending on the bonding state of isoprene, which are cis bond units, trans bond units, 1,2-vinyl bond units, and 3,4-vinyl bond units. For improving the tensile strength of a molded film such as a dip-molded product to be obtained, the content proportion of the cis bond units in the isoprene units contained in the synthetic polyisoprene is preferably 70 wt % or more, more preferably 90 wt % or more, further preferably 95 wt % or more, with respect to all isoprene units.

The weight-average molecular weight of the synthetic polyisoprene is preferably 10,000 to 5,000,000, more preferably 500,000 to 5,000,000, further preferably 800,000 to 3,000,000, in terms of standard polystyrene by gel permeation chromatography. Adjusting the weight-average molecular weight of the synthetic polyisoprene to the aforementioned range tends to improve the tensile strength of the molded film such as a dip-molded product and facilitate the production of the synthetic polyisoprene latex.

Further, the polymer/Mooney viscosity (ML1+4 at 100° C.) of the synthetic polyisoprene is preferably 50 to 80, more preferably 60 to 80, further preferably 70 to 80.

As a method for obtaining a synthetic polyisoprene latex, there are (1) a method for producing a synthetic polyisoprene latex by emulsifying a solution or a microsuspension of a synthetic polyisoprene dissolved or finely dispersed in an organic solvent, in water in the presence of an anionic surfactant, followed by removal of the organic solvent, as required, and (2) a method for directly producing a synthetic polyisoprene latex by emulsion polymerization or suspension polymerization of isoprene alone or a mixture of isoprene with an ethylenically unsaturated monomer that is copolymerizable with isoprene, in the presence of an anionic surfactant. The aforementioned production method (1) is preferable since the synthetic polyisoprene with cis bond units at a high proportion in the isoprene units can be used, and a molded film such as a dip-molded product having excellent mechanical properties such as tensile strength is easily obtained. In the case of producing a synthetic polyisoprene latex by the production method (1), a synthetic polyisoprene latex may be obtained by mixing the medium-chain fatty acid glyceride, which will be described below, in a solution or a fine suspension of a synthetic polyisoprene dissolved or finely dispersed in an organic solvent and emulsifying the solution or fine suspension of synthetic polyisoprene mixed with the medium-chain fatty acid glyceride in water in the presence of an anionic surfactant, followed by removal of the organic solvent, as required. The synthetic polyisoprene latex thus obtained may be used as the latex composition of the present invention.

Examples of the organic solvent used in the aforementioned production method (1) include aromatic hydrocarbon solvents such as benzene, toluene, and xylene; alicyclic hydrocarbon solvents such as cyclopentane, cyclopentene, cyclohexane, and cyclohexene; aliphatic hydrocarbon solvents such as pentane, hexane, and heptane; and halogenated hydrocarbon solvents such as methylene chloride, chloroform, and ethylene dichloride. Among these, alicyclic hydrocarbon solvents are preferable, and cyclohexane is particularly preferable.

The amount of the organic solvent to be used is preferably 2,000 parts by weight or less, more preferably 20 to 1,500 parts by weight, further preferably 500 to 1,500, with respect to 100 parts by weight of the synthetic polyisoprene.

Examples of the anionic surfactants to be used in the aforementioned production method (1) include fatty acid salts such as sodium laurate, potassium myristate, sodium palmitate, potassium oleate, sodium linolenate, and sodium rosinate; alkylbenzenesulfonates such as sodium dodecylbenzenesulfonate, potassium dodecylbenzenesulfonate, sodium decylbenzenesulfonate, potassium decylbenzenesulfonate, sodium cetylbenzenesulfonate, and potassium cetylbenzenesulfonate; alkyl sulfosuccinates such as sodium di(2-ethylhexyl) sulfosuccinate, potassium di(2-ethylhexyl) sulfosuccinate, and sodium dioctyl sulfosuccinate; alkyl sulfate ester salts such as sodium lauryl sulfate and potassium lauryl sulfate; polyoxyethylene alkyl ether sulfate ester salts such as sodium polyoxyethylene lauryl ether sulfate and potassium polyoxyethylene lauryl ether sulfate; and monoalkyl phosphates such as sodium lauryl phosphate and potassium lauryl phosphate.

Among these anionic surfactants, fatty acid salts, alkylbenzenesulfonates, alkyl sulfosuccinates, alkyl sulfate ester salts, and polyoxyethylene alkyl ether sulfate ester salts are preferable, and fatty acid salts and alkylbenzenesulfonates are particularly preferable.

Further, use of at least one selected from the group consisting of alkylbenzenesulfonates, alkyl sulfosuccinates, alkyl sulfate ester salts, and polyoxyethylene alkyl ether sulfate ester salts in combination with fatty acid salts is preferable, and use of alkylbenzenesulfonates in combination with fatty acid salts is particularly preferable, because a slight amount of the residual polymerization catalyst (particularly, aluminum and titanium) derived from the synthetic polyisoprene can be more efficiently removed and generation of aggregates is suppressed in the production of the latex composition. Here, as fatty acid salts, sodium rosinate and potassium rosinate are preferable, and as alkylbenzenesulfonates, sodium dodecylbenzenesulfonate and potassium dodecylbenzenesulfonate are preferable. Further, one of these surfactants may be used alone, or two or more of them may be used in combination.

As described above, use of at least one selected from the group consisting of alkylbenzenesulfonates, alkyl sulfosuccinates, alkyl sulfate ester salts, and polyoxyethylene alkyl ether sulfate ester salts in combination with fatty acid salts allows the obtained latex to contain the at least one selected from alkylbenzenesulfonates, alkyl sulfosuccinates, alkyl sulfate ester salts, and polyoxyethylene alkyl ether sulfate ester salts, and fatty acid salts.

Further, in the aforementioned production method (1), surfactants other than the anionic surfactants may be used in combination, and examples of the surfactants other than the anionic surfactants include copolymerizable surfactants such as sulfoesters of $\alpha,\beta$-unsaturated carboxylic acids, sulfate esters of $\alpha,\beta$-unsaturated carboxylic acids, sulfoalkyl aryl ethers.

Further, nonionic surfactants such as polyoxyethylene alkyl ethers, polyoxyethylene alkyl phenol ethers, polyoxyethylene alkyl esters, and polyoxyethylene sorbitan alkyl esters may be used in combination, as long as coagulation by the coagulant that is used in dip molding is not inhibited.

The amount of anionic surfactants to be used in the aforementioned production method (1) is preferably 0.1 to 50 parts by weight, more preferably 0.5 to 30 parts by weight, with respect to 100 parts by weight of the synthetic polyisoprene. In the case of using two or more surfactants, the total amount of the surfactants to be used preferably falls within the aforementioned range. That is, for example, in the case of using at least one selected from alkylbenzenesulfonates, alkyl sulfosuccinates, alkyl sulfate ester salts, and polyoxyethylene alkyl ether sulfate ester salts in combination with fatty acid salts, the total amount of these surfactants to be used preferably falls within the aforementioned range. An excessively small amount of the anionic surfactants used may possibly cause a large amount of aggregates in emulsification, or conversely, an excessively large amount thereof facilitates foaming and may possibly cause pinholes in a molded film such as a dip-molded product to be obtained.

Further, in the case of using at least one selected from alkylbenzenesulfonates, alkyl sulfosuccinates, alkyl sulfate ester salts, and polyoxyethylene alkyl ether sulfate ester salts in combination with fatty acid salts as anionic surfactants, the ratio of these surfactants to be used is preferably adjusted to a range of 1:1 to 10:1, more preferably to a range of 1:1 to 7:1, as a weight ratio of "fatty acid salts":"total of at least one surfactant selected from alkylbenzenesulfonates, alkyl sulfosuccinates, alkyl sulfate ester salts, and polyoxyethylene alkyl ether sulfate ester salts". An excessively large ratio of the at least one surfactant selected from alkylbenzenesulfonates, alkyl sulfosuccinates, alkyl sulfate ester salts, and polyoxyethylene alkyl ether sulfate ester salts to be used may possibly cause intense foaming when handling the synthetic polyisoprene, thereby making operations such as long-term standing and addition of a defoamer necessary, which may possibly lead to a decrease in workability and an increase in cost.

The amount of water to be used in the aforementioned production method (1) is preferably 10 to 1,000 parts by weight, more preferably 30 to 500 parts by weight, most preferably 50 to 100, with respect to 100 parts by weight of the organic solvent solution of the synthetic polyisoprene. Examples of the type of water to be used include hard water, soft water, deionized water, distilled water, zeolite water and the like, and soft water, deionized water, and distilled water are preferable.

Examples of the method for adding monomers include a method of adding monomers to be used into a reaction container in a lump, a method of adding monomers continuously or intermittently as polymerization proceeds, a method of partially adding monomers to allow a reaction to proceed to a specific conversion rate and then adding the residual monomers continuously or intermittently for polymerization, and the like. Any one of the methods may be employed. In the case of mixing monomers and thereafter adding the monomers continuously or intermittently, the composition of the mixture may be constant or varied. Further, as the monomers, various monomers to be used may be mixed in advance and then added into the reaction container or may be separately added into the reaction container.

As the device that emulsifies the solution or the microsuspension of the synthetic polyisoprene dissolved or finely dispersed in the organic solvent, in water, in the presence of anionic surfactants, devices that are commercially available in general as emulsifying machines or dispersers can be used without specific limitation. The method for adding the anionic surfactants to the solution or the microsuspension of the synthetic polyisoprene is not specifically limited, and the anionic surfactants may be added in advance to either water, or the solution or the microsuspension of the synthetic polyisoprene, or both of them, or may be added in a lump or dividedly to the emulsified liquid during the emulsification operation.

Examples of the emulsifying device include batch emulsifying machines such as the product name "Homogenizer" (manufactured by IKA Works), the product name "POLYTRON" (manufactured by Kinematica AG), and the product name "TK AUTO-HOMO MIXER" (manufactured by Tokushu Kika Kogyo Co., Ltd.); continuous emulsifying machines such as the product name "TK PIPELINE-HOMO MIXER" (manufactured by Tokushu Kika Kogyo Co., Ltd.), the product name "Colloid mill" (manufactured by Shinko Pantec Co., Ltd.), the product name "SLASHER" (manufactured by NIPPON COKE & ENGINEERING CO., LTD.), the product name "Trigonal wet grinder" (manufactured by Mitsui Miike Chemical Engineering Machinery, Co., Ltd.), the product name "CAVITRON" (manufactured by Eurotec, Ltd.), the product name "MILDER" (manufactured by Pacific Machinery & Engineering Co., Ltd.), and the product name "FINE FLOW MILL" (manufactured by Pacific Machinery & Engineering Co., Ltd.); high-pressure emulsifying machines such as the product name "Microfluidizer" (manufactured by MIZUHO INDUSTRIAL CO., LTD.), the product name "NANOMIZER" (manufactured by NANOMIZER Inc.), and the product name "APV GAULIN" (manufactured by Manton-Gaulin Company); membrane emulsifying machines such as the product name "Membrane emulsifying machine" (manufactured by REICA Co., Ltd.); vibratory emulsifying machines such as the product name "VIBROMIXER" (manufactured by REICA Co., Ltd.); and ultrasonic emulsifying machines such as the product name "Ultrasonic homogenizer" (manufactured by Branson Ultrasonics Corporation). The conditions for the emulsification operation by such emulsifying devices are not specifically limited, and the processing temperature, the processing time, and the like, may be appropriately determined so that a desired dispersion state is achieved.

In the aforementioned production method (1), the organic solvent is desirably removed from the emulsion obtained by the emulsification operation.

As the method for removing the organic solvent from the emulsion, methods that can reduce the content of the organic solvent (preferably, an alicyclic hydrocarbon solvent) in the synthetic polyisoprene latex to be obtained to 500 weight ppm or less are preferable, and methods such as vacuum distillation, normal pressure distillation, water vapor distillation, and centrifugation can be employed, for example.

In the aforementioned method (1), the organic solvent is desirably removed from the emulsion obtained by the aforementioned emulsification operation, to obtain a synthetic polyisoprene latex. The method for removing the organic solvent from the emulsion is not specifically limited as long as it is a method that can reduce the total content of the alicyclic hydrocarbon solvent and the aromatic hydrocarbon solvent as organic solvents in the synthetic polyisoprene latex to be obtained to 500 weight ppm or less, and methods such as vacuum distillation, normal pressure distillation, water vapor distillation, and centrifugation can be employed therefor.

Further, concentration operation may be applied, as needed, by a method such as vacuum distillation, normal pressure distillation, centrifugation, and membrane concentration, after the removal of organic solvents, in order to increase the solid content concentration of the synthetic polyisoprene latex. Centrifugation is particularly preferably performed, since the solid content concentration of the synthetic polyisoprene latex can be increased, and the amount of the surfactants remaining in the synthetic polyisoprene latex can be reduced.

The centrifugation is preferably performed, for example, using a continuous centrifuge, under the conditions in which the centrifugal force is preferably 100 to 10,000 G, the solid content concentration of the synthetic polyisoprene latex before centrifugation is preferably 2 to 15 wt %, the feed flow rate into the centrifuge is preferably 500 to 1700 Kg/hr, and the back pressure (gauge pressure) of the centrifuge is preferably 0.03 to 1.6 MPa. The synthetic polyisoprene latex can be obtained as a light liquid after the centrifugation. Further, the amount of the surfactants remaining in the synthetic polyisoprene latex can be thereby reduced.

The solid content concentration of the synthetic polyisoprene latex is preferably 30 to 70 wt %, more preferably 40 to 70 wt %. When the solid content concentration is excessively low, the solid content concentration of the latex composition, which will be described below, decreases, and therefore the film thickness of the dip-molded product, which will be described below, decreases, so that the dip-molded product easily breaks. Conversely, when the solid content concentration is excessively high, the viscosity of the synthetic polyisoprene latex increases, so that transfer through a pipe or stirring within a preparation tank may be made difficult in some cases.

The volume average particle size of the synthetic polyisoprene latex is preferably 0.1 to 10 μm, more preferably 0.5 to 3 μm, further preferably 0.5 to 2.0 μm. Adjusting the volume average particle size to the aforementioned range can make the latex viscosity appropriate to facilitate handling and can suppress formation of a film on the surface of the latex during storage of the synthetic polyisoprene latex.

Further, the synthetic polyisoprene latex may contain additives that are generally contained in the field of latex, such as pH adjusters, defoamers, preservatives, crosslinking agents, chelating agents, oxygen scavengers, dispersants, and anti-aging agents.

Examples of the pH adjusters include alkali metal hydroxides such as sodium hydroxide and potassium hydroxide; alkali metal carbonates such as sodium carbonate and potassium carbonate; alkali metal hydrogen carbonates such as sodium hydrogen carbonate; ammonia; and organic amine compounds such as trimethylamine and triethanolamine, and alkali metal hydroxides and ammonia are preferable.

Further, in the case of using a styrene-isoprene-styrene block copolymer (SIS) as the conjugated diene polymer, a styrene-isoprene-styrene block copolymer latex (SIS latex) can be used as the conjugated diene polymer latex. In the SIS, the character "S" represents a styrene block, and the character "I" represents an isoprene block.

The method for producing the SIS latex is not specifically limited, but a method for producing a SIS latex by emulsifying a solution or a microsuspension of a SIS dissolved or finely dispersed in an organic solvent, in water, in the presence of surfactants and removing the organic solvent, as required, is preferable. In the case of producing a synthetic polyisoprene latex by this method, the medium-chain fatty acid glyceride, which will be described below, is mixed in a solution or a fine suspension of SIS dissolved or finely dispersed in an organic solvent, and the solution or fine suspension of SIS mixed with the medium-chain fatty acid glyceride is emulsified in water in the presence of surfactants, followed by removal of the organic solvent, as required, to obtain a SIS latex. The SIS latex thus obtained may be used as the latex composition of the present invention.

The SIS can be obtained by conventionally known methods such as block copolymerization of isoprene and styrene in an inert polymerization solvent using an active organic metal such as n-butyl lithium as an initiator. The polymer solution of the obtained SIS may be used as it is for producing the SIS latex but can be used for producing the SIS latex by extracting a solid SIS from the polymer solution and thereafter dissolving the solid SIS in an organic solvent.

At this time, impurities such as the residue of the polymerization catalyst remaining in the polymer solution after the synthesis may be removed. Further, an anti-aging agent, which will be described below, may be added into the solution during the polymerization or after the polymerization. Further, a commercially available solid SIS also can be used.

As the organic solvent, the same organic solvent as that for the aforementioned synthetic polyisoprene can be used, and aromatic hydrocarbon solvents and alicyclic hydrocarbon solvents are preferable, and cyclohexane and toluene are particularly preferable.

The amount of the organic solvent to be used is generally 50 to 2,000 parts by weight, preferably 250 to 2,000 parts by weight, more preferably 400 to 1,250 parts by weight, with respect to 100 parts by weight of the SIS.

As the surfactants, the same surfactants as described above for the aforementioned synthetic polyisoprene can be mentioned, for example. Anionic surfactants are suitable, and potassium rosinate, sodium rosinate, and sodium dodecylbenzene sulfonate are particularly preferable. Further, one of these surfactants may be used alone, or two or more of them may be used in combination.

The amount of surfactants to be used is preferably 0.1 to 50 parts by weight, more preferably 0.5 to 30 parts by weight, with respect to 100 parts by weight of the SIS. When this amount is excessively small, the stability of the latex tends to be poor. Conversely, when the amount is excessively large, foaming easily occurs, which may possibly cause a problem in dip molding.

The amount of water to be used in the aforementioned method for producing the SIS latex is preferably 10 to 1,000 parts by weight, more preferably 30 to 500 parts by weight, most preferably 50 to 100 parts by weight, with respect to 100 parts by weight of the organic solvent solution of the SIS. Examples of the type of water to be used include hard water, soft water, deionized water, distilled water, and zeolite water and the like. Further, polar solvents typified by alcohols such as methanol may be used in combination with water.

As a method for adding monomers, the same methods as described above for the aforementioned synthetic polyisoprene can be mentioned, for example. As a device that emulsifies an organic solvent solution or a microsuspension of SIS in water in the presence of a surfactant, the same devices as described above for the aforementioned synthetic polyisoprene can be mentioned, for example. The method for adding the surfactants is not specifically limited, and the surfactants may be added in advance to either water, or the organic solvent solution or the microsuspension of the SIS, or both of them, or may be added to the emulsified liquid during the emulsification operation at one time or several times.

In the aforementioned method for producing a SIS latex, the SIS latex is preferably obtained by removing the organic solvent from the emulsion obtained by the emulsification operation. The method for removing the organic solvent from the emulsion is not specifically limited, and methods such as vacuum distillation, normal pressure distillation, water vapor distillation, and centrifugation can be employed.

Further, in order to increase the solid content concentration of the SIS latex, concentration operation may be applied after the removal of the organic solvent, as needed, by methods such as vacuum distillation, normal pressure distillation, centrifugation, and membrane concentration.

The solid content concentration of the SIS latex is preferably 30 to 70 wt %, more preferably 50 to 70 wt %. When the solid content concentration is excessively low, the solid content concentration of the latex composition, which will be described below, decreases, and therefore the film thickness of the dip-molded product decreases, so that the dip-molded product easily breaks. Conversely, when the solid content concentration is excessively high, the viscosity of the SIS latex increases, so that transfer through a pipe or stirring within a preparation tank is made difficult.

Further, the SIS latex may contain additives that are generally contained in the field of latex, such as pH adjusters, defoamers, preservatives, crosslinking agents, chelating agents, oxygen scavengers, dispersants, and anti-aging agents. As the pH adjusters, the same pH adjusters as described above for the synthetic polyisoprene can be mentioned, and alkali metal hydroxides and ammonia are preferable.

The content of styrene units in the styrene block of the SIS contained in the thus obtained SIS latex is preferably 70 to 100 wt %, more preferably 90 to 100 wt %, further preferably 100 wt %, with respect to all monomer units.

Further, the content of isoprene units in the isoprene block of the SIS is preferably 70 to 100 wt %, more preferably 90 to 100 wt %, further preferably 100 wt %, with respect to all monomer units.

The content ratio of the styrene units to isoprene units in the SIS is generally in the range of 1:99 to 90:10, preferably 3:97 to 70:30, more preferably 5:95 to 50:50, further preferably 10:90 to 30:70, as a weight ratio of "styrene units: isoprene units".

The weight-average molecular weight of the SIS is preferably 10,000 to 1,000,000, more preferably 50,000 to 500,000, further preferably 100,000 to 300,000, in terms of standard polystyrene by gel permeation chromatography. Adjusting the weight-average molecular weight of the SIS to the aforementioned range tends to improve the balance of the tensile strength and the flexibility of the molded film such as a dip-molded product and facilitate the production of the SIS latex.

The volume average particle size of the latex particles (SIS particles) in the SIS latex is preferably 0.1 to 10 μm, more preferably 0.5 to 3 μm, further preferably 0.5 to 2.0 μm. Adjusting the volume average particle size of the latex particles to the aforementioned range makes the latex viscosity appropriate to facilitate handling and can suppress formation of a film on the surface of the latex during storage of the SIS latex.

Further, in the case of using a nitrile group-containing conjugated diene copolymer as the conjugated diene polymer, a latex of the nitrile group-containing conjugated diene copolymer can be used as the conjugated diene polymer latex.

The latex of the nitrile group-containing conjugated diene copolymer is a latex of a copolymer famed by copolymerization of ethylenically unsaturated nitrile monomers with conjugated diene monomers and may be a latex of a copolymer famed by copolymerization of the aforementioned monomers with other ethylenically unsaturated monomers that are copolymerizable with the aforementioned monomers and are used, as required, in addition to the aforementioned monomers.

Examples of the conjugated diene monomers include 1,3-butadiene, isoprene, 2,3-dimethyl-1,3-butadiene, 2-ethyl-1,3-butadiene, 1,3-pentadiene, chloroprene, and the like. Among these, 1,3-butadiene and isoprene are preferable, and 1,3-butadiene is more preferable. One of these conjugated diene monomers can be used alone, or two or more of them can be used in combination. The content proportion of conjugated diene monomer units famed by the conjugated diene monomers in the nitrile group-containing conjugated diene copolymers is preferably 56 to 78 wt %, more preferably 56 to 73 wt %, further preferably 56 to 68 wt %. Adjusting the content of conjugated diene monomer units to the aforementioned range can allow a molded film such as a dip-molded product to be obtained to be more excellent in texture and elongation, while having sufficient tensile strength.

The ethylenically unsaturated nitrile monomers are not specifically limited as long as they are ethylenically unsaturated monomers containing a nitrile group, but examples thereof include acrylonitrile, methacrylonitrile, fumaronitrile, α-chloroacrylonitrile, α-cyanoethylacrylonitrile, and the like. Among these, acrylonitrile and methacrylonitrile are preferable, and acrylonitrile is more preferable. One of these ethylenically unsaturated nitrile monomers can be used alone, or two or more of them can be used in combination. The content proportion of ethylenically unsaturated nitrile monomer units famed by the ethylenically unsaturated nitrile monomers in the nitrile group-containing conjugated diene copolymer is preferably 20 to 40 wt %, more preferably 25 to 40 wt %, further preferably 30 to 40 wt %. Adjusting the content of the ethylenically unsaturated nitrile monomer units to the aforementioned range can allow a molded film such as a dip-molded product to be obtained to be more excellent in texture and elongation, while having sufficient tensile strength.

Examples of the other ethylenically unsaturated monomers that are copolymerizable with the conjugated diene monomers and the ethylenically unsaturated nitrile monomers include ethylenically unsaturated carboxylic acid monomers that are ethylenically unsaturated monomers containing a carboxyl group; vinyl aromatic monomers such as styrene, alkyl styrene, and vinylnaphthalene; fluoroalkyl vinyl ethers such as fluoroethyl vinyl ether; ethylenically unsaturated amide monomers such as (meth)acrylamide, N-methylol (meth)acrylamide, N,N-dimethylol (meth)acrylamide, N-methoxymethyl (meth)acrylamide, and N-propoxymethyl (meth)acrylamide; ethylenically unsaturated carboxylic acid ester monomers such as methyl (meth) acrylate, ethyl (meth)acrylate, butyl (meth)acrylate, 2-ethylhexyl (meth)acrylate, trifluoroethyl (meth)acrylate, tetrafluoropropyl (meth)acrylate, dibutyl maleate, dibutyl fumarate, diethyl maleate, methoxymethyl (meth)acrylate, ethoxyethyl (meth)acrylate, methoxyethoxyethyl (meth) acrylate, cyanomethyl (meth)acrylate, 2-cyanoethyl (meth) acrylate, 1-cyanopropyl (meth)acrylate, 2-ethyl-6-cyanohexyl (meth)acrylate, 3-cyanopropyl (meth)acrylate, hydroxyethyl (meth)acrylate, hydroxypropyl (meth)acrylate, glycidyl (meth)acrylate, and dimethylaminoethyl (meth)acrylate; crosslinkable monomers such as divinylbenzene, polyethylene glycol di(meth)acrylate, polypropylene glycol di(meth)acrylate, trimethylolpropane tri(meth)acrylate, and pentaerythritol (meth)acrylate; and the like. One of these ethylenically unsaturated monomers can be used alone, or two or more of them can be used in combination.

The ethylenically unsaturated carboxylic acid monomers are not specifically limited as long as they are ethylenically unsaturated monomers containing a carboxyl group, but examples thereof include ethylenically unsaturated monocarboxylic acid monomers such as acrylic acid and methacrylic acid; ethylenically unsaturated polyvalent carboxylic acid monomers such as itaconic acid, maleic acid, and fumaric acid; ethylenically unsaturated polyvalent carboxylic acid anhydrides such as maleic anhydride and citraconic anhydride; ethylenically unsaturated polyvalent carboxylic acid partial ester monomers such as monobutyl fumarate, monobutyl maleate, and mono-2-hydroxypropyl maleate; and the like. Among these, ethylenically unsaturated monocarboxylic acid is preferable, and methacrylic acid is particularly preferable. The ethylenically unsaturated carboxylic acid monomers are also used as alkali metal salts or ammonium salts. Further, one of these ethylenically unsaturated carboxylic acid monomers can be used alone, or two or more of them can be used in combination. The content proportion of ethylenically unsaturated carboxylic acid monomer units famed by the ethylenically unsaturated carboxylic acid monomers in the nitrile group-containing conjugated diene copolymer is preferably 2 to 5 wt %, more preferably 2 to 4.5 wt %, further preferably 2.5 to 4.5 wt %. Adjusting the content of the ethylenically unsaturated carboxylic acid monomer units to the aforementioned range can allow a molded film such as a dip-molded product to be obtained to be more excellent in texture and elongation, while having sufficient tensile strength.

The content proportion of other monomer units famed by the other ethylenically unsaturated monomers in the nitrile group-containing conjugated diene copolymer is preferably 10 wt % or less, more preferably 5 wt % or less, further preferably 3 wt % or less.

The nitrile group-containing conjugated diene copolymer is obtained by copolymerization of a monomer mixture containing the aforementioned monomers, but a method of copolymerization by emulsion polymerization is preferable.

For the emulsion polymerization method, a conventionally known method can be employed.

In the emulsion polymerization of the monomer mixture containing the aforementioned monomers, polymerization auxiliary materials that are generally used such as emulsifiers, polymerization initiators, and molecular weight modifiers can be used. A method for adding these polymerization auxiliary materials is not specifically limited, and any method such as initial one-time addition, divided addition, and continuous addition may be employed.

The emulsifiers are not specifically limited, and examples thereof can include nonionic emulsifiers such as polyoxyethylene alkyl ether, polyoxyethylene alkyl phenol ether, polyoxyethylene alkyl ester, and polyoxyethylene sorbitan alkyl ester; anionic emulsifiers such as alkylbenzene sulfonates including potassium dodecylbenzene sulfonate, sodium dodecylbenzene sulfonate, and the like, higher alcohol sulfate salts, and alkyl sulfosuccinates; cationic emulsifiers such as alkyl trimethyl ammonium chloride, dialkyl ammonium chloride, and benzyl ammonium chloride; copolymerizable emulsifiers such as sulfoesters of $\alpha,\beta$-unsaturated carboxylic acids, sulfate esters of $\alpha,\beta$-unsaturated carboxylic acids, and sulfoalkyl aryl ethers; and the like. Among these, anionic emulsifiers are preferable, alkylbenzene sulfonates are more preferable, and potassium dodecylbenzene sulfonate and sodium dodecylbenzene sulfonate are particularly preferable. One of these emulsifiers can be used alone, or two or more of them can be used in combination. The amount of the emulsifiers to be used is preferably 0.1 to 10 parts by weight with respect to 100 parts by weight of the monomer mixture.

The polymerization initiators are not specifically limited, but examples thereof can include inorganic peroxides such as sodium persulfate, potassium persulfate, ammonium persulfate, potassium superphosphate, and hydrogen peroxide; organic peroxides such as diisopropylbenzene hydroperoxide, cumene hydroperoxide, t-butyl hydroperoxide, 1,1,3,3-tetramethylbutyl hydroperoxide, 2,5-dimethylhexane-2,5-dihydroperoxide, di-t-butyl peroxide, di-$\alpha$-cumyl peroxide, acetyl peroxide, isobutyryl peroxide, and benzoyl peroxide; azo compounds such as azobisisobutyronitrile, azobis-2,4-dimethylvaleronitrile, and methyl azobisisobutyrate; and the like. One of these polymerization initiators can be used alone, or two or more of them can be used in combination. The amount of the polymerization initiators to be used is preferably 0.01 to 10 parts by weight, more preferably 0.01 to 2 parts by weight, with respect to 100 parts by weight of the monomer mixture.

Further, peroxides initiators can be used in combination with reductants as redox polymerization initiators. The reductants are not specifically limited, but examples thereof include compounds containing reduced metal ions such as ferrous sulfate and cuprous naphthenate; sulfonic acid compounds such as sodium methanesulfonate; amine compounds such as dimethyl aniline; and the like. One of these reductants can be used alone, or two or more of them can be used in combination. The amount of the reductants to be used is preferably 3 to 1000 parts by weight with respect to 100 parts by weight of peroxides.

The amount of water to be used in the emulsion polymerization is preferably 80 to 600 parts by weight, particularly preferably 100 to 200 parts by weight, with respect to 100 parts by weight of all monomers to be used.

As a method for adding monomers, a method of adding monomers to be used into a reaction container in a lump, a method of adding monomers continuously or intermittently as polymerization proceeds, a method of partially adding monomers to allow reaction to proceed to a specific conversion rate and then adding the residual monomers continuously or intermittently for polymerization, and the like can be mentioned, for example. Any one of the methods may be employed. In the case of mixing monomers and thereafter adding the monomers continuously or intermittently, the composition of the mixture may be constant or varied. Further, as the monomers, various monomers to be used may be mixed in advance and then added into the reaction container or may be separately added into the reaction container.

Further, polymerization auxiliary materials such as chelating agents, dispersants, pH adjusters, oxygen scavengers, and particle size modifiers can be used, as required, and both the type and the amount of these polymerization auxiliary materials to be used are not specifically limited.

The polymerization temperature during the emulsion polymerization is not specifically limited but is generally 3 to 95° C., preferably 5 to 60° C. The polymerization time is about 5 to 40 hours.

The monomer mixture is subjected to emulsion polymerization as described above, and the polymerization reaction is stopped by cooling the polymerization system or adding a polymerization terminator at the time when a predetermined polymerization conversion rate is reached. The polymerization conversion rate at which the polymerization reaction is stopped is preferably 90 wt % or more, more preferably 93 wt % or more.

The polymerization terminator is not specifically limited, but examples thereof include hydroxylamine, hydroxyamine sulfate, diethylhydroxylamine, hydroxyaminesulfonic acid and alkali metal salts thereof, sodium dimethyldithiocarbamate, hydroquinone derivatives, catechol derivatives, and aromatic hydroxydithiocarboxylic acids such as hydroxydimethylbenzenethiocarboxylic acid, hydroxydiethylbenzenedithiocarboxylic acid, and hydroxydibutylbenzenedithiocarboxylic acid, and alkali metal salts thereof, and the like. The amount of the polymerization terminator to be used is preferably 0.05 to 2 parts by weight with respect to 100 parts by weight of the monomer mixture.

After the polymerization reaction is stopped, unreacted monomers are removed, as needed, and the solid content concentration and the pH are adjusted, so that the latex of the nitrile group-containing conjugated diene copolymer can be obtained.

Further, anti-aging agents, preservatives, antibacterial agents, dispersants, and the like may be appropriately added to the latex of the nitrile group-containing conjugated diene copolymer, as required.

The number-average particle size of the latex of the nitrile group-containing conjugated diene copolymer is preferably 60 to 300 nm, more preferably 80 to 150 nm. The particle size can be adjusted to a desired value by a method of regulating the amount of the emulsifiers and polymerization initiators to be used, and the like.

As the conjugated diene polymer latex to be used in the present invention, a latex of a synthetic polyisoprene, a styrene-isoprene-styrene block copolymer (SIS), a nitrile group-containing conjugated diene copolymer, and the like can be used, as described above, but there is no limitation to these, and a butadiene polymer latex, a styrene-butadiene copolymer latex, and the like may be used.

The butadiene polymer latex may be a homopolymer of 1,3-butadiene as conjugated diene monomers or may be a latex of a copolymer formed by copolymerization of 1,3-butadiene as conjugated diene monomers with other ethylenically unsaturated monomers that are copolymerizable with 1,3-butadiene.

Further, the styrene-butadiene copolymer latex may be a latex of a copolymer formed by copolymerization of 1,3-butadiene as conjugated diene monomers with styrene or may be a latex of a copolymer famed by copolymerization of the aforementioned monomers with other ethylenically unsaturated monomers that are copolymerizable with the aforementioned monomers and are used, as required, in addition to the aforementioned monomers.

Medium-Chain Fatty Acid Glyceride

The latex composition of the present invention contains a medium-chain fatty acid glyceride in an amount within a range of 1 to 40 parts by weight with respect to 100 parts by weight of the conjugated diene polymer contained in the latex, in addition to the aforementioned conjugated diene polymer latex.

In the case where a latex composition to be obtained is famed into a molded film such as a dip-molded product, adjusting the content proportion of the medium-chain fatty acid glyceride in the latex composition to the aforementioned specific range can improve not only the flexibility of the molded film by the action of the medium-chain fatty acid glyceride as a plasticizer but also the tear strength of the molded film by the action of the medium-chain fatty acid glyceride, according to the present invention. If a long-chain fatty acid glyceride is mixed in the conjugated diene polymer latex, the long-chain fatty acid glyceride is not sufficiently dissolved in the latex, and the effects of improving the flexibility and the tear strength of the molded film to be obtained cannot be obtained. Further, if a short-chain fatty acid glyceride is mixed in the conjugated diene polymer latex, the short-chain fatty acid glyceride is dissolved in the latex, but the effects of improving the flexibility and the tear strength of the molded film to be obtained by the action of the short-chain fatty acid glyceride would be insufficient. In contrast, excellent effects of improving the flexibility and the tear strength of the molded film to be obtained can be obtained according to the present invention by mixing the medium-chain fatty acid glyceride in the conjugated diene polymer latex and controlling the content proportion of the medium-chain fatty acid glyceride to the aforementioned range.

The content proportion of the medium-chain fatty acid glyceride in the latex composition of the present invention is 1 to 40 parts by weight, preferably 1 to 30 parts by weight, more preferably 1 to 15 parts by weight, with respect to 100 parts by weight of the conjugated diene polymer contained in the latex. An excessively low content proportion of the medium-chain fatty acid glyceride reduces not only the flexibility but also the tear strength of a molded film such as a dip-molded product to be obtained. An excessively high content proportion of the medium-chain fatty acid glyceride improves the flexibility of a molded film such as a dip-molded product to be obtained, but excessively improved flexibility rather reduces the tear strength and the tensile strength.

The medium-chain fatty acid glyceride to be used in the present invention needs only to be obtained by esterifying glycerin with a medium-chain fatty acid and may be any one of medium-chain fatty acid monoglycerides, medium-chain fatty acid diglycerides, and medium-chain fatty acid triglycerides. Among these, medium-chain fatty acid diglycerides and medium-chain fatty acid triglycerides are preferable, medium-chain fatty acid triglycerides are particularly preferable.

The medium-chain fatty acid forming the medium-chain fatty acid glyceride to be used in the present invention is not specifically limited, but examples thereof include linear fatty acids such as caproic acid ($C_{H3}$ $(C_{H2})_4$COOH) enanthic acid ($C_{H3}$ $(C_{H2})_5$COOH) caprylic acid ($C_{H3}$ $(C_{H2})_6$COOH) pelargonic acid ($C_{H3}(C_{H2})_7$COOH), capric acid ($C_{H3}$ $(C_{H2})_8$COOH), undecyl acid ($C_{H3}(C_{H2})_9$COOH), lauric acid ($C_{H3}(C_{H2})_{10}$COOH), tridecane acid ($C_{H3}(C_{H2})_{11}$COOH), myristic acid ($C_{H3}(C_{H2})_{12}$COOH), pentadecane acid ($C_{H3}$ $(C_{H2})_{13}$COOH), palmitic acid ($C_{H3}(C_{H2})_{14}$COOH), heptadecane acid ($C_{H3}(C_{H2})_{15}$COOH), stearic acid ($C_{H3}$ $(C_{H2})_{16}$COOH), nonadecylic acid ($C_{H3}(C_{H2})_{17}$COOH), arachidic acid ($C_{H3}$ $(C_{H2})_{18}$COOH), behenic acid ($C_{H3}$ $(C_{H2})_{20}$COOH), lignoceric acid ($C_{H3}$ $(C_{H2})_{22}$COOH), oleic acid, linoleic acid, linolenic acid, arachidonic acid, and behenic acid; oil fatty acids such as tallow fatty acid; and the like. Among these, fatty acids having 6 to 18 carbon atoms are preferable, fatty acids having 6 to 13 carbon atoms are more preferable, fatty acids having 7 to 13 carbon atoms are further preferable, and fatty acids having 8 to 10 carbon atoms are particularly preferable. In the case where the medium-chain fatty acid glyceride is a medium-chain fatty acid diglyceride or a medium-chain fatty acid triglyceride, the medium-chain fatty acids forming the medium-chain fatty acid glyceride to be used may be of one type alone or may be of two or more types in combination.

For the latex composition of the present invention, the method for mixing the medium-chain fatty acid glyceride needs only to be a method that eventually yields a mixture of the conjugated diene polymer latex and the medium-chain fatty acid glyceride and is not specifically limited, but examples thereof include a method of obtaining the conjugated diene polymer latex and thereafter mixing a medium-chain fatty acid glyceride with the conjugated diene polymer latex, a method of mixing a medium-chain fatty acid glyceride in advance with a solution or a fine suspension of a conjugated diene polymer dissolved or finely dispersed in an organic solvent, thereafter emulsifying the solution or the fine suspension of the conjugated diene polymer mixed with the medium-chain fatty acid glyceride in water, followed by removal of the organic solvent, as required, to obtain a conjugated diene polymer latex mixed with the medium-chain fatty acid glyceride, and using the conjugated diene polymer latex as the latex composition of the present invention, and the like. Among these, a method of obtaining a conjugated diene polymer latex and thereafter mixing a medium-chain fatty acid glyceride in the conjugated diene polymer latex is preferable, since the medium-chain fatty acid glyceride is easily dissolved, and the medium-chain fatty acid glyceride is more easily mixed.

Latex Composition

The latex composition of the present invention contains the aforementioned conjugated diene polymer latex and the aforementioned medium-chain fatty acid glyceride, and the content proportion of the medium-chain fatty acid glyceride falls within the aforementioned range.

The latex composition of the present invention needs only to contain the conjugated diene polymer latex and the medium-chain fatty acid glyceride but preferably further contains a crosslinking agent.

Examples of the crosslinking agent include sulfurs such as powder sulfur, flowers of sulfur, precipitated sulfur, colloid sulfur, surface-treated sulfur, and insoluble sulfur; and sulfur-containing compounds such as sulfur chloride, sulfur dichloride, morpholine disulfide, alkyl phenol disulfide, N,N'-dithio-bis(hexahydro-2H-azepinone-2), phosphorus-containing polysulfide, polymer polysulfide, and 2-(4'-morpholinodithio)benzothiazole. Among these, sulfurs can be preferably used. One of the crosslinking agents may be used alone, or two or more of them may be used in combination.

The content of crosslinking agents is not specifically limited but is preferably 0.1 to 10 parts by weight, more preferably 0.2 to 3 parts by weight, with respect to 100 parts by weight of the conjugated diene polymer. Adjusting the content of crosslinking agents to the aforementioned range can further enhance the tensile strength of a molded film such as a dip-molded product to be obtained.

The latex composition of the present invention preferably further contains a crosslinking accelerator.

As the crosslinking accelerator, crosslinking accelerators that are generally used in dip molding can be used, and examples thereof include dithiocarbamic acids such as diethyldithiocarbamic acid, dibutyldithiocarbamic acid, di-2-ethylhexyldithiocarbamic acid, dicyclohexyldithiocarbamic acid, diphenyldithiocarbamic acid, and dibenzyldithiocarbamic acid, and zinc salts thereof; 2-mercaptobenzothiazole, zinc 2-mercaptobenzothiazole, 2-mercaptothiazoline, dibenzothiazyl disulfide, 2-(2,4-dinitrophenylthio)benzothiazole, diethylthio carbaylthio)benzothiazole, 2-(2,6-dimethyl-4-morpholinothio)benzothiazole, 2-(4'-morpholino dithio) benzothiazole, 4-morpholinyl-2-benzothiazyl disulfide, 1,3-bis(2-benzothiazyl mercaptomethyl)urea, and the like. Zinc diethyldithiocarbamate, 2 zinc dibutyldithiocarbamate, and zinc 2-mercaptobenzothiazole are preferable. One of the crosslinking accelerators may be used alone, or two or more of them may be used in combination.

The content of crosslinking accelerators is preferably 0.05 to 5 parts by weight, more preferably 0.1 to 2 parts by weight, with respect to 100 parts by weight of the conjugated diene polymer. Adjusting the content of crosslinking accelerators to the aforementioned range can further enhance the tensile strength of a molded film such as a dip-molded product to be obtained.

Further, the latex composition of the present invention preferably further contains zinc oxide.

The content of the zinc oxide is not specifically limited but is preferably 0.1 to 5 parts by weight, more preferably 0.2 to 2 parts by weight, with respect to 100 parts by weight of the conjugated diene polymer. Adjusting the content of the zinc oxide to the aforementioned range can further enhance the tensile strength of a molded film such as a dip-molded product to be obtained while achieving good emulsification stability.

The latex composition of the present invention can further contain compounding agents including anti-aging agents; dispersants; reinforcers such as carbon black, silica, and talc; fillers such as calcium carbonate and clay; ultraviolet absorbers; and plasticizers, as required.

Examples of the anti-aging agents include phenolic anti-aging agents containing no sulfur atoms such as 2,6-di-4-methylphenol, 2,6-di-t-butylphenol, butylhydroxyanisole, 2,6-di-t-butyl-α-dimethylamino-p-cresol, octadecyl-3-(3,5-di-t-butyl-4-hydroxyphenyl)propionate, styrenated phenol, 2,2'-methylene-bis(6-α-methyl-benzyl-p-cresol), 4,4'-methylenebis(2,6-di-t-butylphenol), 2,2'-methylene-bis(4-methyl-6-t-butylphenol), alkylated bisphenol, and a butylated reaction product of p-cresol with dicyclopentadiene; thiobisphenol anti-aging agents such as 2,2'-thiobis-(4-methyl-6-t-butylphenol), 4,4'-thiobis-(6-t-butyl-o-cresol), and 2,6-di-t-butyl-4-(4,6-bis(octylthio)-1,3,5-triazin-2-ylamino)phenol; phosphite ester anti-aging agents such as tris(nonylphenyl) phosphite, diphenylisodecyl phosphite, and tetraphenyl dipropylene glycol diphosphite; sulfur ester anti-aging agents such as dilauryl thiodipropionate; amine anti-aging agents such as phenyl-α-naphthyl amine, phenyl-β-naphthyl amine, p-(p-toluenesulfonylamide)-diphenylamine, 4,4'-(α,α-dimethylbenzyl)diphenylamine, N,N-diphenyl-p-phenylenediamine, N-isopropyl-N'-phenyl-p-phenylenediamine, and butyl aldehyde-aniline condensate; quinoline anti-aging agents such as 6-ethoxy-2,2,4-trimethyl-1,2-dihydroquinoline; and hydroquinone anti-aging agents such as 2,5-di-(t-amyl)hydroquinone. One of these anti-aging agents can be used alone, or two or more of them can be used in combination.

The content of the anti-aging agents is preferably 0.05 to 10 parts by weight, more preferably 0.1 to 5 parts by weight, with respect to 100 parts by weight of the conjugated diene polymer.

The method for mixing various compounding agents in the latex composition of the present invention is not specifically limited, but examples thereof include a method of obtaining a latex composition containing the conjugated diene polymer latex and the medium-chain fatty acid glyceride as described above and thereafter mixing various compounding agents to be mixed, as required, in the latex composition using a disperser such as ball mills, kneaders, and dispersers, a method of preparing an aqueous dispersion of ingredients other than the conjugated diene polymer latex using the aforementioned disperser and thereafter mixing the aqueous dispersion in the conjugated diene polymer latex, and the like.

The solid content concentration of the latex composition of the present invention is preferably 15 to 65 wt %, more preferably 15 to 45 wt %.

In the case where the latex composition of the present invention contains a crosslinking agent, the latex composition of the present invention is preferably aged (precrosslinked) before dip molding, for enhancing the mechanical properties of a molded film such as a dip-molded product to be obtained. The precrosslinking time is not specifically limited and depends also on the precrosslinking temperature but is preferably 1 to 14 days, more preferably 1 to 7 days. The precrosslinking temperature is preferably 20 to 40° C.

Then, after the precrosslinking, the latex composition is preferably stored at a temperature of 10 to 30° C. until the dip molding. If the latex composition is stored at high temperature, the tensile strength of a molded film such as a dip-molded product to be obtained may possibly decrease in some cases.

Molded Film

The molded film of the present invention is a molded product in the form of a film composed of the latex composition of the present invention. The film thickness of the molded film of the present invention is preferably 0.03 to 0.50 mm, more preferably 0.05 to 0.40 mm, particularly preferably 0.05 to 0.30 mm.

The molded film of the present invention is not specifically limited but is suitably a dip-molded product obtained by dip-molding the latex composition of the present invention. The dip molding is a method of immersing a mold in the latex composition, depositing the composition on the surface of the mold, then pulling the mold out of the composition, and thereafter drying the composition deposited on the surface of the mold. The mold before the immersion in the latex composition may be preheated. Further, before the mold is immersed in the latex composition or after the mold is pulled out of the latex composition, a coagulant can be used, as required.

Specific examples of the method for using the coagulant include a method of attaching the coagulant to the mold by immersing, in a coagulant solution, the mold before the immersion in the latex composition (anode coagulant dipping), and a method of immersing the mold on which the latex composition has been deposited in a coagulant solution (Teague coagulant dipping), and the anode coagulant dipping is preferable in that a dip-molded product with less unevenness in thickness is obtained.

Specific examples of the coagulant include water-soluble polyvalent metal salts including metal halides such as barium chloride, calcium chloride, magnesium chloride, zinc chloride, and aluminum chloride; nitrates such as barium nitrate, calcium nitrate, and zinc nitrate; acetates such as barium acetate, calcium acetate, and zinc acetate; and sulfates such as calcium sulfate, magnesium sulfate, and aluminum sulfate. Among these, calcium salts are preferable, and calcium nitrate is more preferable. One of these water-soluble polyvalent metal salts can be used alone, or two or more of them can be used in combination.

The coagulant can be generally used as a solution of water, alcohol, or a mixture thereof and is preferably used in the form of an aqueous solution. The aqueous solution may further contain water-soluble organic solvents such as methanol and ethanol, and nonionic surfactants. The concentration of the coagulant differs depending on the type of the water-soluble polyvalent metal salts but is preferably 5 to 50 wt %, more preferably 10 to 30 wt %.

The mold after being pulled out of the latex composition is generally heated to dry the deposit famed on the mold. The drying conditions may be appropriately selected.

In the case where the latex composition contains a crosslinking agent, the dip-molded layer obtained is generally subjected to heat treatment for crosslinking. Before the heat treatment, immersion in water, preferably hot water at 30 to 70° C., for about 1 to 60 minutes may be performed to remove water-soluble impurities (such as excess emulsifiers and coagulants). Water-soluble impurities may be removed after the heat treatment of the dip-molded layer but are preferably removed before the heat treatment since water-soluble impurities can be removed more efficiently.

The dip-molded layer is crosslinked by heat treatment generally at a temperature of 80 to 150° C., preferably for 10 to 130 minutes. As a heating method, methods by external heating using infrared rays or heated air, or internal heating using high-frequency waves can be employed. Among these, external heating using heated air is preferable.

Then, a dip-molded product is obtained as a molded film by detaching the dip-molded layer from the mold for dip molding. As a detaching method, methods of peeling the film from the mold for forming by hand and peeling the film by water pressure or pressure of compressed air can be employed. After the detachment, heat treatment at a temperature of 60 to 120° C. for 10 to 120 minutes may be further performed.

The molded film of the present invention may be obtained by any method other than the method of dip-molding the latex composition of the present invention as long as the method enables formation of the latex composition of the present invention into a film (such as coating method).

The molded film of the present invention containing the dip-molded product of the present invention is obtained using the latex composition of the present invention and thus has excellent flexibility and also excellent tear strength. Therefore, the molded film of the present invention can be used particularly suitably, for example, as a glove. In the case where the molded film forms a glove, inorganic fine particles such as talc and calcium carbonate or organic fine particles such as starch particles may be spread on the surface of the glove, an elastomer layer containing fine particles may be famed on the surface of the glove, or the surface layer of the glove may be chlorinated, in order to prevent the close contact on the contact surface of the molded film with itself and improve slippage when putting it on and taking it off.

Further, the molded film of the present invention containing the dip-molded product of the present invention can be used as medical supplies such as baby bottle nipples, droppers, tubes, water pillows, balloon stalls, catheters, and condoms; toys such as balloons, dolls, and balls; industrial supplies such as pressure molding bags and gas storage bags; fingerstalls; and the like, other than the aforementioned glove.

Packaging Structure

The packaging structure of the present invention has a structure famed by bonding a first sheet substrate and a second sheet substrate that are coated with the latex composition of the present invention to each other to formula laminate, the structure being capable of containing an article to be packaged. Specifically, in the packaging structure of the present invention, the first sheet substrate and the second sheet substrate form a structure in which the first sheet substrate and the second sheet substrate are bonded to each other by being pressed while the first sheet substrate and the second sheet substrate are in contact with each other with their surfaces coated with the latex composition (latex-coated surfaces) being opposed to each other and an article to be packaged being interposed therebetween, as required, so that the article to be packaged can be packaged. The article to be packaged is not specifically limited but examples thereof include various articles to be packaged that are desired to be sterilized like medical supplies such as bandages. The first sheet substrate and the second sheet substrate are not specifically limited, but examples thereof include paper materials such as glassine paper, high-density polyethylene non-woven fabrics, polyolefin films, polyester films, and the like. Among these, paper materials are preferable, and glassine paper is particularly preferable because of excellent handleability (reasonable ease of bending) and inexpensiveness.

EXAMPLES

Hereinafter, the present invention will be specifically described with reference to the Examples. However, the present invention is not limited to these examples. The "part(s)" and "%" below are based on weight, unless otherwise specified. Various physical properties were measured as follows.

Solid Content Concentration 2 g of each sample was accurately weighed (weight: X2) into an aluminum dish (weight: X1), followed by drying in a hot air dryer at 105° C. for 2 hours. Subsequently, after cooling in a desiccator, the weight thereof including the aluminum dish was measured (weight: X3), to calculate the solid content concentration according to the following calculation formula.

Solid content concentration (wt %)=(X3−X1)×100/X2

Tensile Strength, Elongation at Break, and 500% Tensile Stress of Dip-Molded Product Based on ASTM D412, a film-like dip-molded product with a film thickness of about 0.2 mm was punched out using a dumbbell (product name "SUPER DUMBBELL (type: SDMK-100C)" manufactured by DUMBBELL CO., LTD.), to produce a test piece for tensile strength measurement. The test piece was stretched using a TENSILON Universal Material Testing Instrument (product name "RTG-1210", manufactured by ORIENTEC CORPORATION) at a tensile speed of 500 mm/min, to measure the tensile strength (unit: MPa) immediately before breaking, the elongation (unit: %) immediately before breaking, and the tensile stress (unit: MPa) at an elongation of 500%. A higher tensile strength and a higher elongation at break are preferable. Further, the lower the tensile stress at 500%, the dip-molded product has more excellent flexibility, which is preferable.

Tear Strength of Dip-Molded Product

Based on ASTM D624-00, a dip-molded product, after being allowed to stand in a constant temperature and humidity chamber at 23° C. and a relative humidity of 50% for 24 hours or more, was punched out using a dumbbell (product name "Die C" manufactured by DUMBBELL CO., LTD.), to produce a test piece for tear strength measurement. The test piece was stretched using a TENSILON Universal Material Testing Instrument (product name "RTG-1210" manufactured by A&D Company, Limited) at a tensile speed of 500 mm/min, to measure the tear strength (unit: N/mm). A higher tear strength is preferable.

Example 1

Preparation of Latex Composition 250 parts (100 parts in terms of synthetic polyisoprene polymer) of a synthetic polyisoprene polymer latex (product name "NIPOL ME1100", manufactured by Zeon Corporation) as the conjugated diene polymer latex was adjusted with an aqueous solution of potassium hydroxide to a solid content concentration of 40% and a pH of 10.5 under stirring, and 5 parts of a medium-chain fatty acid glyceride (a-1) (product name "MASESTER-E7000", manufactured by Chuo Kasei Co., Ltd., a medium-chain fatty acid triglyceride using a fatty acid having 8 to 10 carbon atoms as a medium-chain fatty acid) was added thereto, followed by stirring at room temperature for 72 hours, to obtain a latex composition. Thereafter, aqueous dispersions of compounding agents respectively containing 1.5 parts of zinc oxide, 1.5 parts of sulfur, 2 parts of an anti-aging agent (product name "Wingstay L", manufactured by Goodyear Tire and Rubber Company), 0.3 parts of zinc diethyldithiocarbamate, 0.5 parts of zinc dibutyldithiocarbamate, and 0.7 parts of zinc mercaptobenzothiazole, in terms of solid content with respect to 100 parts of the synthetic polyisoprene polymer in the latex composition were added thereto. Thereafter, the latex composition was aged for 48 hours in a constant-temperature water bath adjusted to 30° C.

Production of Dip-Molded Product

A commercially available ceramic hand mold (manufactured by SHINKO CERAMICS CO., LTD.) was washed, followed by preheating in an oven at 70° C. Thereafter, the hand mold was immersed in an aqueous solution of a coagulant containing 18 wt % of calcium nitrate and 0.05 wt % of polyoxyethylene lauryl ether (product name "EMULGEN 109P", manufactured by Kao Corporation) for 5 seconds and was taken out of the aqueous solution of the coagulant. Subsequently, the hand mold was dried in an oven at 70° C. for 30 minutes or more, thereby allowing the coagulant to adhere to the hand mold, so that the hand mold was coated with the coagulant.

Thereafter, the hand mold coated with the coagulant was taken out of the oven and was immersed in the latex composition for 10 seconds. Subsequently, the hand mold was air-dried at room temperature for 10 minutes and was immersed in hot water at 60° C. for 5 minutes to elute water-soluble impurities, thereby forming a dip-molded layer on the hand mold. Thereafter, the dip-molded layer famed on the hand mold was crosslinked by heating in an oven under the conditions of a temperature of 130° C. for 30 minutes, followed by cooling to room temperature, and was separated from the hand mold by spreading talc, to obtain a dip-molded product (rubber glove). Then, the tensile strength, the elongation at break, the stress at 500% elongation, and the tear strength were each measured for the dip-molded product (rubber glove) obtained according to the aforementioned method. Table 1 shows the results.

Example 2

The preparation of a latex composition and the production of a dip-molded product were performed in the same manner as in Example 1 except that the amount of the medium-chain fatty acid glyceride (a-1) added in the latex composition was changed to 14 parts, and the same evaluation was performed. Table 1 shows the results.

Example 3

The preparation of a latex composition and the production of a dip-molded product were performed in the same manner as in Example 1 except that 14 parts of a medium-chain fatty acid glyceride (a-2) (product name "SUNSOFT No. 700P-2", manufactured by Taiyo Kagaku Co., Ltd., a medium-chain fatty acid monoglyceride using caprylic acid having 8 carbon atoms as a medium-chain fatty acid) was used instead of 5 parts of the medium-chain fatty acid glyceride (a-1), and the same evaluation was performed. Table 1 shows the results.

Example 4

Production of SIS Latex 1250 parts (100 parts of SIS and 1150 parts of cyclohexane) of a cyclohexane solution of a styrene-isoprene-styrene block copolymer (SIS) (product name "QUINTAC 3620", manufactured by Zeon Corporation) was prepared. Further, 1250 parts of an aqueous solution of a surfactant containing 0.8 parts of an aqueous solution of potassium rosinate was prepared.

Subsequently, the total amount of the cyclohexane solution of the SIS and the total amount of the aqueous solution of the surfactant (1250 parts of the aqueous solution of the surfactant containing 0.8 parts of the aqueous solution of potassium rosinate) were put into a container made of SUS304, followed by stirring and mixing, and then emulsification treatment was applied thereto using a homogenizer (product name "MILDER MEN-303V", manufactured by Pacific Machinery & Engineering Co., Ltd.), to obtain an emulsified liquid.

Thereafter, the emulsified liquid was transferred to a tank for solvent removal, cyclohexane was distilled off from the emulsified liquid in the tank for solvent removal, to adjust the solid content concentration of the emulsified liquid to 10%. Subsequently, aggregates in the emulsified liquid were removed using a 200-mesh stainless steel wire mesh.

Thereafter, a rotor MN was set in a cooling centrifuge (type "H-2000B", manufactured by KOKUSAN Co., Ltd.), and the emulsified liquid was transferred to a 500-ml centrifuge tube provided in the cooling centrifuge, to perform centrifugation operation under the conditions of a set temperature of 20° C. and a rotational speed of 4,000 G for 20 minutes. A light liquid was scraped out from the centrifuge tube immediately after the rotation of the centrifugation operation was stopped, and the light liquid was obtained as a SIS latex. The solid content concentration of the SIS latex obtained was 55%.

Preparation of Latex Composition and Production of Dip-Molded Product

The preparation of a latex composition and the production of a dip-molded product were performed in the same manner as in Example 1 except that 250 parts (100 parts in terms of SIS) of the SIS latex was used as the conjugated diene polymer latex instead of 250 parts (100 parts in terms of synthetic polyisoprene polymer) of the synthetic polyisoprene polymer latex, and the same evaluation was performed. Table 1 shows the results.

Example 5

Production of Nitrile Group-Containing Conjugated Diene Copolymer Latex 13.5 parts of acrylonitrile, 33.75 parts of 1,3-butadiene, and 2.75 parts of methacrylic acid, as initial polymerization monomers, which account for a total of 50 parts, 0.5 parts of t-dodecyl mercaptan (tDM) and 95 parts of deionized water as molecular weight modifiers, 1.0 part of sodium dodecylbenzene sulfonate (DBS) as an emulsifier, 0.2 parts of potassium persulfate as a polymerization initiator, and 0.1 parts of sodium ethylenediaminetetraacetate (EDTA) as a reductant were put into a nitrogen-substituted pressure-resistant polymerization reactor. The temperature in the polymerization system was raised to 35° C. to start polymerization reaction. At the time when the polymerization conversion rate reached 50%, a 10% aqueous solution of 1.0 part of sodium dodecylbenzene sulfonate as an additional emulsifier was added in a lump. After the completion of the addition of the additional emulsifier (10% aqueous solution of sodium dodecylbenzene sulfonate), an emulsion obtained by emulsifying 13.5 parts of acrylonitrile, 33.75 parts of 1,3-butadiene, and 2.75 parts of methacrylic acid, which account for a total of 50 parts (residual monomers), and 0.4 parts of t-dodecyl mercaptan with 15.0 parts of deionized water and 0.5 parts of sodium dodecylbenzene sulfonate was continuously added to the polymerization system over 270 minutes. The polymerization conversion rate at the time of the completion of the continuous addition was 60%. Thereafter, the polymerization was continued until the polymerization conversion rate of all monomers reached 97%, and then the polymerization reaction was stopped by adding 0.1 parts of diethylhydroxylamine, to obtain the latex of the nitrile group-containing conjugated diene copolymer.

Preparation of Latex Composition and Production of Dip-Molded Product

After distilling off unreacted monomers, the latex of the nitrile group-containing conjugated diene copolymer obtained was adjusted to a solid content concentration of 45% and a pH of 8.3, and 5 parts of the medium-chain fatty acid triglyceride (a-1) used in Example 1 was added thereto, to obtain a latex composition. The latex composition obtained was adjusted to a solid content concentration of 25%, and 8.66 parts of a dispersion of a vulcanizing agent prepared by mixing 1 part of sulfur, 1.5 parts of zinc oxide, 0.5 parts of zinc diethyl carbamate, 0.03 parts of potassium hydroxide, and 5.63 parts of water, with respect to 100 parts of the nitrile group-containing conjugated diene copolymer in the latex composition, was mixed therein. Thereafter, the latex composition adjusted to a solid content concentration of 25% and a pH of 10.0 by adding appropriate amounts of a 5% aqueous solution of potassium hydroxide and deionized water was aged at 30° C. for one day. Using the latex composition after the aging, a dip-molded product was produced in the same manner as in Example 1, and the tensile strength, the elongation at break, and the stress at 500% elongation were each measured according to the aforementioned method. Table 2 shows the results.

Comparative Example 1

The preparation of a latex composition and the production of a dip-molded product were performed in the same manner as in Example 1 except that the medium-chain fatty acid glyceride (a-1) was not used, and the same evaluation was performed. Table 1 shows the results.

Comparative Example 2

The preparation of a latex composition and the production of a dip-molded product were performed in the same manner as in Example 1 except that the amount of the medium-chain fatty acid glyceride (a-1) added in the latex composition was changed to 50 parts, and the same evaluation was performed. Table 1 shows the results.

Comparative Example 3

The preparation of a latex composition and the production of a dip-molded product were performed in the same manner as in Example 1 except that the amount of the medium-chain fatty acid glyceride (a-1) added in the latex composition was changed to 0.5 parts, and the same evaluation was performed. Table 1 shows the results.

Comparative Example 4

The preparation of a latex composition and the production of a dip-molded product were performed in the same manner as in Example 4 except that the medium-chain fatty acid glyceride (a-1) was not used, and the same evaluation was performed. Table 1 shows the results.

Comparative Example 5

The preparation of a latex composition and the production of a dip-molded product were performed in the same manner as in Example 5 except that the medium-chain fatty acid glyceride (a-1) was not used, and the same evaluation was performed. Table 2 shows the results.

TABLE 1

| | | Example | | | | Comparative Example | | | |
|---|---|---|---|---|---|---|---|---|---|
| | | 1 | 2 | 3 | 4 | 1 | 2 | 3 | 4 |
| Composition of latex composition | | | | | | | | | |
| Synthetic polyisoprene | (parts) | 100 | 100 | 100 | | 100 | 100 | 100 | |
| Styrene-isoprene-styrene block copolymer (SIS) | (parts) | | | | 100 | | | | 100 |
| Medium-chain fatty acid glyceride (a-1) (triglyceride using medium-chain fatty acid having 8 to 10 carbon atoms) | (parts) | 5 | 14 | | 14 | | 50 | 0.5 | |
| Medium-chain fatty acid glyceride (a-2) (monoglyceride using medium-chain fatty acid having 8 to 10 carbon atoms) | (parts) | | | 14 | | | | | |
| Evaluation | | | | | | | | | |
| 500% Tensile stress | (MPa) | 1.2 | 1.0 | 1.5 | 1.1 | 1.8 | 0.6 | 1.8 | 1.9 |
| Tear strength | (N/mm) | 19.5 | 22.0 | 18.8 | 18.0 | 15.2 | 6.0 | 15.4 | 16.3 |
| Tensile strength | (MPa) | 23.1 | 22.3 | 20.5 | 20.8 | 24.2 | 8.0 | 23.3 | 19.8 |
| Elongation at break | (%) | 1014 | 1072 | 1023 | 987 | 986 | 2000 | 1050 | 1008 |

TABLE 2

| | | Example 5 | Comparative Example 5 |
|---|---|---|---|
| Composition of latex composition | | | |
| Nitrile group-containing conjugated diene copolymer | (parts) | 100 | 100 |
| Medium-chain fatty acid glyceride (a-1) (triglyceride using medium-chain fatty acid having 8 to 10 carbon atoms) | (parts) | 5 | |
| Evaluation | | | |
| 500% tensile stress | (MPa) | 4.2 | 5.4 |
| Tensile strength | (MPa) | 24.0 | 24.2 |
| Elongation at break | (%) | 744 | 725 |

From Table 1, each dip-molded product produced using the latex composition containing a conjugated diene polymer (synthetic polyisoprene, or styrene-isoprene-styrene block copolymer) latex and a medium-chain fatty acid glyceride, wherein the content proportion of the medium-chain fatty acid glyceride was 1 to 40 parts by weight with respect to 100 parts by weight of the conjugated diene polymer (synthetic polyisoprene or styrene-isoprene-styrene block copolymer) had excellent flexibility and high tear strength due to low 500% tensile stress and further had high tensile strength and high elongation at break (Examples 1 to 4).

Likewise, from Table 2, the dip-molded product produced using the latex composition using a nitrile group-containing conjugated diene copolymer as the conjugated diene polymer and containing the latex of the nitrile group-containing conjugated diene copolymer and a medium-chain fatty acid glyceride, wherein the content proportion of the medium-chain fatty acid glyceride was 1 to 40 parts by weight with respect to 100 parts by weight of the nitrile group-containing conjugated diene copolymer had excellent flexibility due to the 500% tensile stress that was lower than in Comparative Example 5 and further had tensile strength and elongation at break that were as high as those in Comparative Example 5 (Example 5). Further, in Example 5, the medium-chain fatty acid glyceride was mixed in the latex composition with the aforementioned content proportion, and therefore the dip-molded product produced is considered to have high tear strength due to the action of the medium-chain fatty acid glyceride, in the same manner as in Examples 1 to 4.

Meanwhile, each dip-molded product produced using the latex composition not containing the medium-chain fatty acid glyceride had poor flexibility due to high 500% tensile stress (Comparative Examples 1, 4, and 5). Moreover, in Comparative Examples 1 and 4, the dip-molded product produced had not only poor flexibility but also low tear strength due to high 500% tensile stress.

Likewise, the dip-molded product produced using the latex composition with excessively low content proportion of the medium-chain fatty acid glyceride also had not only poor flexibility but also low tear strength due to high 500% tensile stress (Comparative Example 3).

Further, the dip-molded product produced using the latex composition with excessively high content proportion of the medium-chain fatty acid glyceride had low tear strength and low tensile strength (Comparative Example 2).

The invention claimed is:

1. A latex composition comprising:
   a conjugated diene polymer latex; and
   a fatty acid glyceride of a fatty acid having 6 to 18 carbon atoms, wherein
   a content proportion of the fatty acid glyceride is 1 to 40 parts by weight with respect to 100 parts by weight of the conjugated diene polymer, and
   the conjugated diene polymer is a synthetic polyisoprene, a styrene-isoprene-styrene block copolymer, or a nitrile group-containing conjugated diene copolymer.

2. The latex composition according to claim 1, wherein the fatty acid glyceride is a fatty acid triglyceride.

3. The latex composition according to claim 1, further comprising
   a crosslinking agent.

4. A molded film consisting of the latex composition according to claim 1.

5. A packaging structure comprising:
   a coating film consisting of the latex composition according to claim 1, the coating film bonding at least a part of a first sheet substrate and at least a part of a second sheet substrate to form a laminate, the packaging structure being capable of containing an article to be packaged between the first sheet substrate and the second sheet substrate.

6. The latex composition according to claim 1, wherein the conjugated diene polymer latex comprises water and a conjugated diene polymer.

7. The latex composition according to claim 1, wherein the content proportion of the fatty acid glyceride is 1 to 30 parts by weight with respect to 100 parts by weight of the conjugated diene polymer.

8. The latex composition according to claim 1, wherein the content proportion of the fatty acid glyceride is 1 to 15 parts by weight with respect to 100 parts by weight of the conjugated diene polymer.

9. The latex composition according to claim 1, which has a solid content concentration of 15 to 65 wt %.

10. The latex composition according to claim 1, which has a solid content concentration of 15 to 45 wt %.

* * * * *